United States Patent
Platzek et al.

(10) Patent No.: US 7,367,224 B2
(45) Date of Patent: May 6, 2008

(54) RHEOMETER AND METHOD FOR TEMPERATURE CONTROL OF ITS MEASURING CHAMBER

(75) Inventors: Wolfgang Platzek, Karlsruhe (DE); Veit Zschuppe, Rimbach (DE)

(73) Assignee: Thermo Electron (Karlsruhe) GmbH, Karlsruhe (DE)

( * ) Notice: Subject to any disclaimer, the term of this patent is extended or adjusted under 35 U.S.C. 154(b) by 0 days.

(21) Appl. No.: 11/244,221

(22) Filed: Oct. 6, 2005

(65) Prior Publication Data

US 2006/0081038 A1 Apr. 20, 2006

(30) Foreign Application Priority Data

Oct. 16, 2004 (DE) .................. 10 2004 050 751

(51) Int. Cl.
*G01N 11/00* (2006.01)
(52) U.S. Cl. .............. 73/54.43; 73/843; 73/54.37; 73/54.39
(58) Field of Classification Search .............. 73/54.43, 73/9, 54.37, 54.39, 843
See application file for complete search history.

(56) References Cited

U.S. PATENT DOCUMENTS

| | | | | | |
|---|---|---|---|---|---|
| 3,531,996 | A | * | 10/1970 | Harris et al. ............ | 73/865.6 |
| 5,481,903 | A | * | 1/1996 | King et al. ............... | 73/54.28 |
| 5,509,298 | A | * | 4/1996 | Cheema ................... | 73/54.41 |
| 5,696,315 | A | * | 12/1997 | Ball ......................... | 73/54.43 |
| 6,571,610 | B1 | * | 6/2003 | Raffer ..................... | 73/54.35 |
| 6,708,554 | B2 | * | 3/2004 | Hettwer et al. .......... | 73/54.43 |
| 2003/0056575 | A1 | * | 3/2003 | Hettwer et al. .......... | 73/54.28 |
| 2005/0199044 | A1 | * | 9/2005 | Doe et al. ................ | 73/54.43 |

* cited by examiner

*Primary Examiner*—Michael Cygan
(74) *Attorney, Agent, or Firm*—Paul Vincent

(57) ABSTRACT

A rheometer has a measuring chamber which is delimited by a measuring chamber wall in which at least one measuring component is disposed for acceptance of a sample. The measuring chamber can have a gas flowing through it whose temperature is controlled in a desired fashion by a first temperature control device. A second temperature control device is also disposed in the measuring chamber wall by means of which the wall of the measuring chamber can be temperature controlled to a desired temperature. To temperature control the sample, the gas flow in the measuring chamber can be switched off or at least highly reduced prior to measurement of the reological characteristic quantities and further temperature control of the measuring chamber is effected by means of the temperature control of the measuring chamber wall.

8 Claims, 1 Drawing Sheet

RHEOMETER AND METHOD FOR TEMPERATURE CONTROL OF ITS MEASURING CHAMBER

This application claims Paris Convention priority of DE 10 2004 050 751.1 filed Oct. 16, 2004 the complete disclosure of which is hereby incorporated by reference.

BACKGROUND OF THE INVENTION

The invention concerns a rheometer having a measuring chamber which is limited or defined by a measuring chamber wall and in which at least one measuring part is disposed for acceptance of a sample, wherein the measuring chamber can have a flow-through gas brought to a control temperature by means of a temperature control device. The invention also concerns a method for temperature control of a rheometer sample disposed in a measurement chamber thereof, wherein the measurement chamber can have a gas flow temperature controlled by a temperature control device.

In order to determine rheological quantities of a sample it is necessary to a compressional or tensile force on and an associated deformation of the sample must be precisely measured with accurately defined ambient conditions. This is done e.g. using a rotational rheometer in which the sample is disposed between two plate-shaped, horizontally disposed measuring components. The measuring components are rotated relative to each other and the resulting reaction forces are measured. In order to minimize ambient influences during the measurement or in order to measure as a function of a predetermined temperature dependence, the measuring components as well as the sample are disposed in a measuring chamber in which the sample is shielding to as great an extent as possible relative to the surrounding environment.

In many applications, the sample must be kept at a predetermined temperature throughout the entire measurement or a predetermined temperature dependence must be followed, e.g. precise temperature control is required. By means of example, it is assumed below that the material sample must be kept at a temperature which is higher than that of the surrounding environment e.g. must be heated.

Conventional devices are provided for warming a gas, in particular air, using a temperature control device and to cause the warmed gas to flow through the measurement chamber until the sample is brought to a desired temperature. In order to keep the sample at this desired temperature throughout the entire measurement, the temperature controlled gas also flows through the measuring chamber during the measurement. This has, however, the associated disadvantage that the gas flows onto the measuring components as well as the sample and exercises a weak force on the measuring components which can falsify the measurement.

If, alternatively, one shuts off all gas flow during the measurement, the sample changes its temperature, since the environment, in particular to the measuring chamber wall, has a different temperature.

The underlying purpose of the invention is to provide a rheometer of the above mentioned kind, as well as a method for temperature control of its measurement chamber, with which a sample can be kept at a predetermined temperature or can follow a predetermined temperature dependence in a precise manner to facilitate accurate measurements at that temperature or during that temperature dependence.

SUMMARY OF THE INVENTION

This object is achieved in accordance with the invention with a rheometer having the features of the independent claim. Towards this end, one provides the measuring chamber with a second temperature control device by means of which the measuring chamber wall can be temperature controlled to a desired temperature.

In accordance with the invention, the fundamental observation is made that the environment of the material sample and in particular of the measuring chamber walls should be temperature controlled by means of a second temperature device in such a fashion that an undesirable temperature change of the material sample can be avoided.

In a rheometer in accordance with the invention, the sample is brought to a desired temperature in a conventional fashion by introducing a gas through the-measuring chamber which is temperature controlled by means of a first temperature controlled device. The wall of the chamber is simultaneously brought to a substantially equal temperature by means of the second temperature control device. In the event that the gas flow is reduced or eliminated to, for example, a gas flow of less than 2% of the preceding gas flow, the temperature measuring chamber acts as an active insulator to prevent a significant temperature change at the sample. It is thereby possible to carry out measurements of rheological quantities without having interfering effects act on the measuring components. By appropriate temperature control of a measuring chamber wall of the rheometer in accordance with the invention, the sample can kept at a constant temperature over a longer period of time.

The second temperature control device is preferentially disposed within the measuring chamber wall and, in particular, embedded therein. It has turned out to be advantageous to configure the second temperature control device as an electric resistive heater whose heating wires or coils are disposed within the measuring chamber wall.

In a preferred embodiment of the invention, the measuring chamber wall is subjected to the temperature control gas regulated by the temperature control device in addition to being subjected to the temperature control by means of the second temperature control device. Towards this end, a pre-chamber can be disposed to surround the measuring chamber on the outer side of the measuring chamber wall through which the temperature control gas, whose temperature dependence is effected by the first temperature control device, can flow before it exits out of the pre-chamber and enters into an opening in the measuring chamber wall. In this manner, inordinately large temperature differences within the measuring chamber wall can be avoided.

In conventional rheometers, one of the measuring components is disposed on a measuring shaft which penetrates through the measuring chamber wall, normally in the upper region. A preferred embodiment of the invention provides that the openings through which the temperature controlled gas can be introduced into the measuring chamber are disposed at least in the end sections of the measuring chamber opposite to the axial extent of the measuring shaft so that a complete flow of the temperature controlled gas through the measuring chamber is guaranteed. Towards this end, the opening should be substantially radial with respect to the extent of the measuring shaft to produce a sufficient mixing of the temperature controlled gas within the measuring chamber.

In a further improvement of the invention, the measuring chamber has a plurality of parts. The measuring chamber parts can be separated from each other or opened in some other fashion in order to facilitated access to measuring components or to the sample. In the closed state of the measuring chamber portions, the measuring chamber is thermally sealed; although slight escape of temperature controlled gas is acceptable in order to facilitate flow through the measuring chambers.

An inert gas, air or, for low temperature regions, in particular evaporated nitrogen have turned out to be advantageous for temperature control of the measuring chamber. A combination of one or more of these components can also be used.

With respect to the method, the above mentioned object is achieved in that the walls of the measuring chamber are temperature controlled by means of a second temperature controlled device and the gas flow in the measuring chamber is shut-off prior to measurement of the reological quantities.

The additional control of the measuring chamber is effected through temperature control of the measuring chamber wall. Further features of the method can be extracted from the above description of the rheometer.

Further details and features of the invention can be extracted from the following description of an embodiment with reference to the associated drawings.

DESCRIPTION OF THE PREFERRED EMBODIMENT

Figure 1:
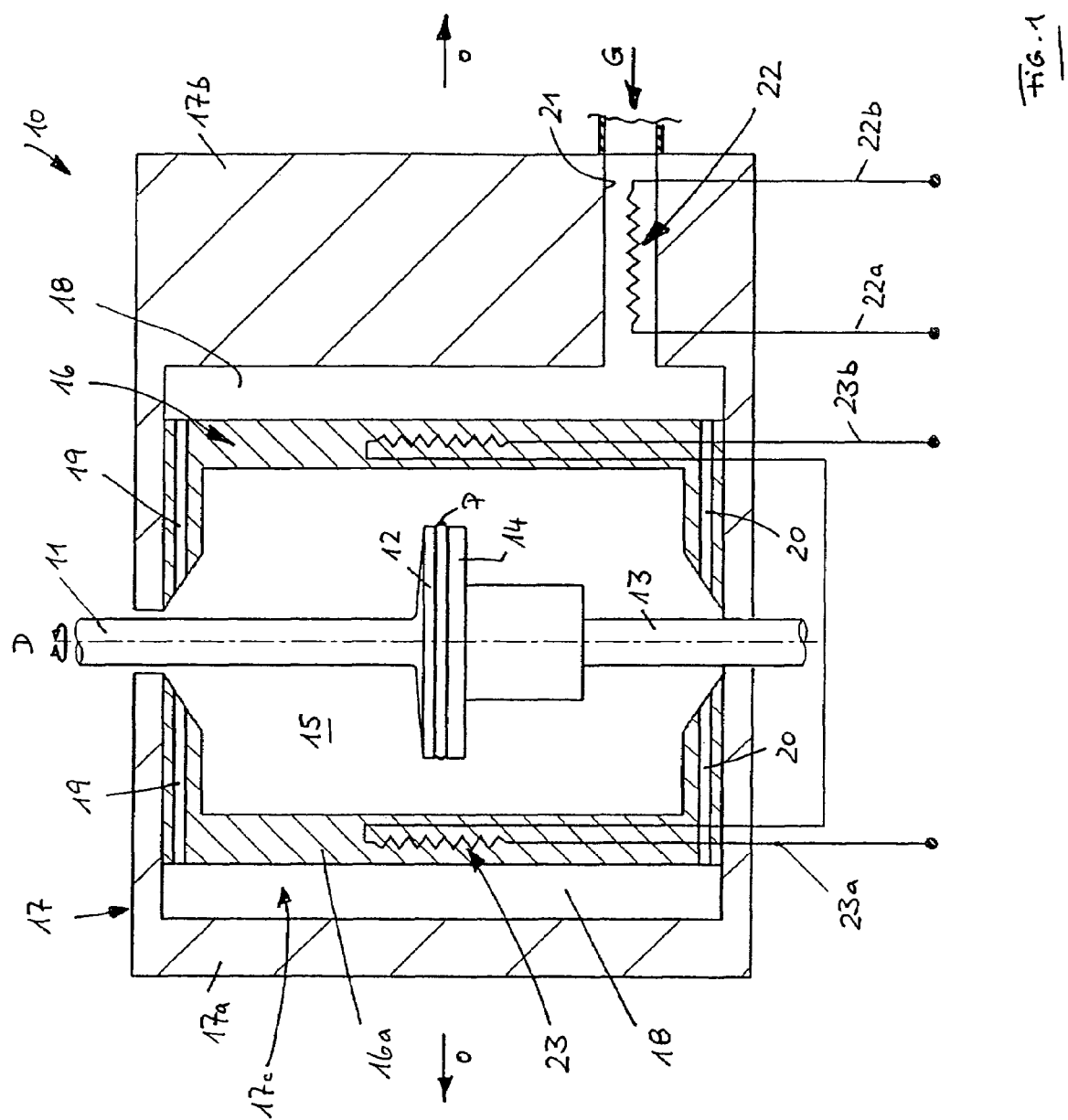
FIG. 1 shows a schematic cross-section through a measuring chamber of a rheometer.

In accordance with FIG. 1, a rheometer 10 has an outer housing 17 which consists essentially of two housing portions 17a and 17b which can be separated from each other in order to open the housing, as indicated by arrow 0. The housing components 17a and 17b define an inner housing region 17c in which a measuring chamber housing 16 is disposed, wherein a pre-chamber 18 is formed about the periphery of the measuring chamber 16 between a cylindrical measuring chamber wall 16a and the inner wall of the outer housing 17.

A measuring chamber 15 is located within the measuring chamber wall 16. A holding rod 13, which is stationary with respect to the frame, penetrates through the lower region of the outer housing 17 and of the measuring chamber housing 16 to project into the measuring chamber 15. The holding rod 13 bears a plate shaped, substantially horizontally directed lower measuring component 14 on its upper free end disposed within the measuring chamber. A likewise plate shaped, substantially horizontally directed upper measuring component 12 is disposed at a separation above the lower measuring component 14 and is held by a measuring shaft 11. The measuring shaft 11 extends in a coaxial direction with respect to the holding rod 13 to penetrate through the outer housing 17 as well as the measurement chamber housing 16 in the upper region thereof and can be caused to rotate, as indicated by the arrow D. The measuring gap is formed between the upper measuring component 12 and the lower measuring component 14 in which a material sample P is disposed.

A gas, temperature controlled at a predetermined temperature, can be introduced into the measuring chamber 15 to control the temperature of the sample P as well as of the measuring chamber 15. The gas is introduced from the outer side of the outer housing 17, as indicated by arrow G, and enters into an inlet channel 21 in the outer housing 17 to pass into the peripherally surrounding pre-chamber 18. In the example shown, a first temperature control device 22 is disposed within the inlet channel 21. A corresponding temperature control device can, however, also be disposed outside of the outer housing 17. The first temperature control device 22 can be formed from an electrical resistive heater which is connected to an electrical voltage source through connecting leads 22a and 22b. The gas, which is temperature controlled in the desired fashion, completely fills the pre-chamber 18 and thereby also temperature controls the outer side of the measuring chamber wall 16a. A plurality of openings 19, 20 extend substantially radially with respect to the measuring shaft 11 and the coaxial holding rod 13 and are distributed about the periphery of the measuring chamber wall 16. A plurality openings 19, 20 are provided in the measuring chamber housing 16 at oppositely disposed end regions of the measuring chamber 15 e.g. proximate the region at which the measuring shaft 11 penetrates through the measuring chamber 16 as well as the outer housing 16 and on the opposite end at which the holding rod 13 penetrates through the measuring chamber housing 16. The temperature controlled gas can flow out of the prechamber 18 through the openings 19, 20 and into the measuring chamber 15.

A second temperature control device 23 is provided for temperature control of the measuring chamber wall 16a and is configured as an electrical resistive heating which can be connected to a voltage source (not shown) by means of connecting leads 23a and 23b. The heating wires of the second temperature control device 13 are completely embedded in the measuring chamber wall 16a.

To prepare a measurement of the sample P, the properly temperature controlled gas flows through the measuring chamber 15 and the measuring chamber wall 16 is simultaneously brought to a corresponding temperature by means of the second temperature control device 23. The gas flow is stopped prior to carrying out the measurement, wherein subsequent constant maintenance of the temperature of the material sample P is effected by means of the temperature control in the measuring chamber wall 16a.

We claim:

1. A rheometer for measuring rheological properties of a sample, the rheometer comprising:
   a housing having means defining a gas inlet;
   a first heating means disposed at said gas inlet defining means to heat a gas as that gas flows through said gas inlet;
   a measuring chamber having a measuring chamber wall, said measuring chamber disposed within and surrounded by said housing, said measuring chamber structured to accommodate the sample; and
   second means for heating said measuring chamber wall to maintain a substantially constant temperature of the sample within said measuring chamber when gas flow through said gas inlet is interrupted or throttled, wherein said housing defines a pre-chamber surrounding said measuring chamber on an outer side thereof, wherein the gas heated by said first heating means flows through said pre-chamber and into said measuring chamber through openings in said measuring chamber wall.

2. The rheometer of claim 1, wherein said second heating means is disposed within said measuring chamber wall.

3. The rheometer of claim 1, wherein said second heating means is an electrical resistance heater.

4. The rheometer of claim 1, wherein said openings are disposed in opposite end sections of said measuring chamber.

5. The rheometer of claim 1, wherein said openings extend substantially radially with respect to a measuring shaft disposed in said measuring chamber.

6. The rheometer of claim 1, wherein said measuring chamber has a plurality of components which can be moved relative to each other to open said measuring chamber.

7. The rheometer of claim 1, wherein the gas is an inert gas, air, nitrogen, or a mixture of a plurality of same.

8. A method for temperature control of a sample disposed in a measuring chamber of a rheometer, the rheometer having a housing surrounding and containing the measuring chamber, the method comprising the steps of:
   a) switching on a first heating device, the first heating device disposed at an inlet opening in the housing to heat gas as that gas flows through that inlet opening towards the measuring chamber;
   b) passing the gas into the measuring chamber following step a);
   c) switching on a second heating device to heat a measuring chamber wall surrounding and defining the measuring chamber;
   d) strongly reducing or switching off the gas flow through the inlet opening;
   e) measuring characteristic rheological quantities of the sample; and
   f) continuing to heat the measuring chamber wall using the second heating device following step d) and during step e) to maintain the sample at a substantially constant temperature.

* * * * *